(12) United States Patent
Weise et al.

(10) Patent No.: US 7,240,528 B2
(45) Date of Patent: Jul. 10, 2007

(54) METHOD AND DEVICE FOR SHAPING AN ORTHODONTIC ARCHWIRE

(75) Inventors: Thomas Weise, Berlin (DE); Ruedger Rubbert, Berlin (DE)

(73) Assignee: Lingualcare, Inc., Dallas, TX (US)

( * ) Notice: Subject to any disclaimer, the term of this patent is extended or adjusted under 35 U.S.C. 154(b) by 120 days.

(21) Appl. No.: 10/992,808

(22) Filed: Nov. 22, 2004

(65) Prior Publication Data

US 2006/0107720 A1  May 25, 2006

(51) Int. Cl.
*B21D 7/12* (2006.01)
*B21D 11/10* (2006.01)
*A61C 3/00* (2006.01)

(52) U.S. Cl. .............................. 72/31.11; 72/307; 433/3
(58) Field of Classification Search ................... 72/307, 72/31.05, 31.1, 306, 31.11; 433/3, 75; 33/513
See application file for complete search history.

(56) References Cited

U.S. PATENT DOCUMENTS

| | | | | |
|---|---|---|---|---|
| 1,103,606 | A | * 7/1914 | Montag | 72/383 |
| 2,566,414 | A | * 9/1951 | Henry | 72/362 |
| 3,352,136 | A | * 11/1967 | Clarke | 72/16.2 |
| 4,184,259 | A | * 1/1980 | Sosnay | 433/4 |
| 4,656,860 | A | 4/1987 | Orthuber | |
| 4,732,025 | A | * 3/1988 | Marlinga et al. | 72/18.5 |
| 5,275,031 | A | * 1/1994 | Whiteside et al. | 72/17.3 |
| 5,431,562 | A | 7/1995 | Andreiko | |
| 6,293,791 | B1 | * 9/2001 | Weinstein | 433/4 |
| 6,612,143 | B1 | 9/2003 | Butscher | |

OTHER PUBLICATIONS

Weichmann, Dirk, A New Bracket System for Lingual Orthodontic Treatment, J Orofac Orthop 2003;64:372-88.
Weichmann, Dirk, A New Bracket System for Lingual Orthodontic Treatment, J Orofac Orthop 2002;63:234-45.
Weichmann, Dirk, et al., Customized Brackets and Archwires for Lingual Orthodontic Treatment, Am J Orthod Dentofacial Orthop 2003:124:593-99.
Mujagic, Magali, et al., Digital Design and Manufacturing of the Lingualcare Bracket System, J Clin. Orthod Jun. 2005;39:6:375-82.
Marketing brochure distributed at German Annual Orthodontic Congress 1994 by Geyer Medizintechnik, Berlin, Germany (facsimile, 8 pages).
Printed advertisment by Geyer Medizintechnik in Congress Program of German Annual Orthodontic Congress 1993 (facsimile. 1 page).

* cited by examiner

*Primary Examiner*—Daniel C. Crane
(74) *Attorney, Agent, or Firm*—Bracewell & Giuliani LLP

(57) ABSTRACT

An apparatus for bending orthodontic wires has means for guiding and holding a wire. In order to prevent forces resulting from compressive or stretching strain during the bending process, one of these means does not apply any longitudinal forces onto the wire by design. In another implementation, the apparatus for bending orthodontic wires has a gimbal-mounted gripper for bending the wire. Furthermore, a method is disclosed for applying two bends at the same longitudinal wire location in two different directions.

22 Claims, 8 Drawing Sheets

METHOD AND DEVICE FOR SHAPING AN ORTHODONTIC ARCHWIRE

CROSS-REFERENCE TO RELATED APPLICATIONS

Not applicable

STATEMENT REGARDING FEDERALLY SPONSORED RESEARCH OR DEVELOPMENT

Not applicable

REFERENCE TO SEQUENCE LISTING, A TABLE, OR A COMPUTER PROGRAM LISTING COMPACT DISK APPENDIX

Not applicable

BACKGROUND OF THE INVENTION

The present invention relates to methods for applying a desired shape to archwires to be used in orthodontic appliances for the straightening of teeth, and more particularly, to the automated manufacture of customized archwires using robotic devices.

The common approach for orthodontic appliances is to bond small metallic parts ("brackets") onto the outer ("labial") side of the teeth, and to insert a wire into the slots of the brackets. The wires are typically preformed off-the-shelf wires, and the brackets are bonded basing on visual judgment by the orthodontist. However, the use of computerized processes in orthodontics increases. Especially when the brackets are bonded to the back side of the teeth ("lingual orthodontics"), the use of computer assisted processes for designing the brackets and manufacturing the wires has achieved a significant market share. Using computerized processes typically results in providing a numeric description of an orthodontic archwire.

Devices for bending orthodontic archwires have been proposed in the prior art. In U.S. Pat. No. 5,431,562, Andreiko et al. describes an apparatus that takes a straight archwire and imparts a simple planar arcuate curvature to the wire. However, the Andreiko et al. wire bending apparatus cannot produce any complex and twists bends in the wire, e.g., bends requiring a combination of translation and rotational motion.

In U.S. Pat. No. 6,612,143 ("Robot and method for bending orthodontic archwires and other medical devices"), Butscher et al. discloses a robot capable of bending fully three-dimensional orthodontic archwires. The device comprises two grippers, one of the grippers being mounted to a six-axis-robot arm and thus moveable. The gripping tools preferably incorporate force sensors which are used to determine overbends needed to get the desired final shape of the archwire. The manufacturing process uses straight pieces of wire and step by step applies bends and/or twists to the wire, thus forming an archwire. The process as described in the '143 patent requires the calculation of the consumed wire length for a bend. Even a slight miscalculation of the consumed wire length for a bend generates significant forces along the longitudinal axis of the wire. Those high forces arising by estimating an improper consumed wire length for a bend will superimpose the bending forces and significantly disturb the desired measurements of those forces.

The patent to Orthuber et al., U.S. Pat. No. 4,656,860 also describes a bending robot for bending archwires. A robot as described in the '860 patent was manufactured and sold as part of a complete orthodontic solution by Geyer Medizintechnik GmbH in Berlin, Germany, but never widely commercialized. The robot consisted of two characteristic design features: a bending cone that could move forwards and backwards to bend the wire, and a rotating cone that could twist the wire. As such, it could only apply torque or bends over the two main axes of a cross section of a rectangular shaped wire. Basing on the embodiment distributed by Geyer Medizintechnik GmbH, a series of three twists and two bends were required to shape an archwire so that it would fit in the slots of two adjacent brackets. This series of twists and bends required as much as 5 mm of wire length between adjacent brackets. This length of wire is greater than that available for closely spaced teeth, especially in lingual orthodontics.

The present invention presents substantial improvements over prior art as disclosed in the cited applications.

BRIEF SUMMARY OF THE INVENTION

A primary objective of the present invention is to provide a reliable and efficient method for applying a permanent customized shape to an orthodontic archwire using robotic devices.

If a device similar to the description in U.S. Pat. No. 6,612,143 is used, it is preferable over the disclosed apparatus to replace one of the grippers with a bushing for supporting and guiding the wire. Such a guide bushing would preferably be adapted to the cross section of the wire in order to allow for precise twists. The design of the bushing would be optimized for low friction. In a preferred embodiment, the bushing is mounted to the base plate of the robot. The moveable arm carries the gripper as described in the '143 patent. The wire would be fed through the bushing. The moveable gripper would grip the wire extending through the bushing and pull a predefined length of the wire out of the bushing, said length basing for instance on best estimates as disclosed in the '143 patent. During the bending process, the discrepancy between the calculated and the actual consumed wire length for the bend would generate longitudinal forces. These forces would cause the wire to slip through the bushing and therefore automatically correct the discrepancy. Only the amount of friction forces between the wire and the bushing would remain, and these forces can be minimized by a variety of means.

In another embodiment, a device as disclosed in U.S. Pat. No. 4,656,860 is used. As implemented by Geyer Medizintechnik GmbH, Berlin, Germany, specific straight portions of the wire are assigned to specific bracket slots. The original implementation of the robot used a sequence of three twists and two bends in order to define a geometry leading from a straight wire portion assigned to a first slot to a straight wire portion assigned to a second slot. While this implementation has specific advantages, it has the big disadvantage of consuming significant wire length. Due to the design of the robot, after each twist action a relevant wire feed is required before the next bend may be applied. Therefore the required total wire length from the end of one bracket slot to the beginning of a second bracket slot quickly adds up to approx. 5 mm, depending on the specific amounts of bends and twists and the specific mechanical layout of the robot. For lingual archwires, this is far too much. Especially the lower front teeth often have a width not exceeding 5 mm, and the arch length of a lingual wire is even shorter that the length of the dental arch. Additionally, a bracket width of 2 mm minimum can be assumed, so that the available length between two brackets is below 3 mm.

In order to overcome this limitation, an alternative command sequence is generated. Instead of applying a twist followed by a bend, two bends at the same location along the wire axis, but in different directions are applied. This has the same effect like the original sequence, but consumes much less wire length. Only one twist between the couple of bends has to be applied in order to adapt the rotational orientation of the wire.

In yet another embodiment of the invention, a modified device is used. Both devices disclosed in the '143 and in the '860 patent have weaknesses in ensuring the desired precision of the applied bends and twists. The device according to the '860 patent clamps the wire only below the point where it is bent. The portion of the wire extending beyond the cone is free and unconstrained; the robot had no control as to the effective deformation of the wire. Therefore, the material properties of the wires to be used have to be calibrated in a tedious process, and very tight material tolerances have to be maintained. The device according to the '143 patent does clamp the wire on both ends of the applied deformation. However, in order to control the precise shape of the bent wire, the residual spring-back forces are measured. This is a process prone to errors, especially since side effects as discussed before will introduce additional disturbances.

The device according to this invention clamps the wire on both ends of the portion to be deformed. Unlike the device disclosed in the '143 patent, it has restricted capabilities with respect to the shapes that may be applied to the wire, but it can be build using a mechanically extraordinarily stiff design. This stiff design is the foundation for the principle of measuring the precision of the applied deformations. After applying the force for the deformation, one of the grippers is decoupled from any driving force, but remains clamped to the wire. Now, the exact location and orientation of the gripper is measured, directly reflecting the new shape of the wire. Depending on the predefined tolerances, the deformation may be refined by subsequent application of corrective forces, or the deformation is accepted. Due to the stiff design, a combination of bends and twists can be applied at one location. Unlike the device disclosed in the '860 patent, the device disclosed in this application it is not limited to bends along a main axis of the cross section.

The device comprises mainly a guide bushing for guiding the wire on one side of the deformation to be applied and a gripper for clamping the wire on the opposite side of the deformation to be applied. While the guide bushing is fixed, the gripper is mounted on three bearings. The first bearing allows rotating the gripper around the longitudinal axis of the wire in order to apply the twisting component of the deformation. The second bearing is mounted around the gripper and the first bearing and allows to apply the bending component to the deformation. The third bearing is mounted around the second bearing and allows to adjust the direction of bending. The gripper is therefore gimbaled. The gripper is also completely balanced around its centers of motion. All three bearings are designed to cause very low friction, and three axes are equipped with contact-free rotary encoders. If the gripper clamps onto the wire, and no external force is applied to the gripper, the rotational angles of the three axes (provided by the rotary encoders) will precisely document the passive or relaxed shape of the wire. If the present shape is not within the tolerances of the nominal shape, corrective movements are to be made by the gripper. These movements can be initiated manually or by actuators. If actuators are used, and the signals of the rotational encoders are processed accordingly, the process shaping the wire could be fully automated, provided that additional means for feeding the wire are present and that the clamping functionality of the gripper is also actuated. In a preferred embodiment, the actuators can be coupled to the axes and fully decoupled while the measurement of the actual wire shape is performed.

DETAILED DESCRIPTION OF THE INVENTION

Six Axis Robot Having One Gripper

Figure 1:
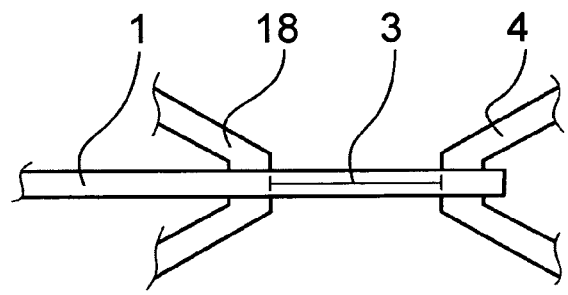
FIG. 1 illustrates a straight piece of wire being held by two grippers. The calculated consumed wire length for the bend is indicated in the center of the wire and equals the distance between the end of the first gripper and the beginning of the second gripper.

The robot as disclosed in U.S. Pat. No. 6,612,143 comprises two grippers, one of the grippers being mounted to a six-axis-robot arm and thus moveable in all six degrees of freedom. The other gripper is fixed to the base plate of the robot. The gripping tools preferably incorporate force sensors which are used to determine overbends needed to get the desired final shape of the archwire. The manufacturing process uses straight pieces of wire and step by step applies bends and/or twists to the wire, thus forming an archwire. The process as described in the '143 patent requires the calculation of the consumed wire length for a bend. In column 16 line 64 ff. it is described how such a calculation can be performed. Also, FIG. 20B displays a proposed algorithm. From the specification it becomes obvious that the exact calculation of the required straight wire length is not possible. Even a slight miscalculation of the consumed wire length for a bend generates significant forces along the longitudinal axis of the wire, since a wire as used for orthodontics purposes may be flexible in the direction transversal to its longitudinal axis, but is extremely stiff in the longitudinal axis. Depending on the veracity of the calculations, the forces generated by estimating an improper consumed wire length for a bend can significantly exceed the forces actually required for bending the wire. This is a very undesired side effect since the whole concept of the '143 patent bases on the precise measurement of forces generated by bending the wire. The high forces arising by estimating an improper consumed wire length for a bend will superimpose the bending forces and significantly disturb the desired measurements of those forces.

The term "bend" as used in this specification and the claims can mean a pure bend, a pure twist or a combination of both. This is in line with the general usage of the term "bend" in orthodontics. A pure twist is referred to as a "3rd order bend" by orthodontists.

Patent '143 describes in great detail the usage of force sensors in order to determine the required overbending of the wire. From the specification it becomes obvious that the proposed process is not very fault tolerant. It can easily be imagined that various influences like longitudinal forces as described above or the mechanical flexibility of an off-the-shelf six-axis-robot will be highly disturbing and may even corrupt proper function.

The calculated length consumed for a bend reflects the distance between the two grippers before the bending process starts, in other words while the wire is still straight.

An exact calculation of the straight wire length consumed for a bend has not yet been introduced. The reason is that if a significant amount of bending forces is applied to a wire, not only bending but also shearing deformations will occur, and accordingly the cross section of the wire will change. Only slightest changes in the cross section can have a great effect on the exact location of the neutral axis. The neutral axis is the zone where no tensile forces and no compression forces are active. Theoretically, the length of the neutral axis as a first approximation is equal to the consumed wire length. However, all calculations and approximations do typically not exactly reflect the true outcome, and toolmakers will always run a couple of tests with the nominal material before they start designing a tool.

The disadvantage of performing a calculation is that due to the longitudinal stiffness of a wire, even a slight miscalculation of the consumed wire length leads to significant longitudinal forces. For instance, if the required wire length for a bend would be 3 mm, and the calculation produces a result of 2.9 mm, an error of 0.1 mm would result. The longitudinal force within a wire portion of stainless steel having a length of 3 mm and a cross section of 0.017"× 0.025" resulting from compression or elongation of 0.1 mm will be approx. 1700N. This exceeds by far the forces that are active in order to bend the wire. The true forces may be lower because the wire will not actually be compressed but bulge, and the mechanical structures of the bending robot will also have certain flexibility. It is obvious, however, that the bending process itself and all force measurements will be significantly superimposed and disturbed by the longitudinal forces.

The solution to this problem is to clamp the wire only on one side of the deformation zone. In a preferred embodiment, a gripper that is mounted to the arm of the six-axis-robot will clamp the wire and perform the bending and twisting movement. On the opposite side of the deformation zone, a low friction guiding bushing will support the wire in order to maintain the integrity of the desired deformation, but will restrict longitudinal movements as little as possible. The calculations of the consumed wire length for a bend can be executed as taught in the '143 patent. However, while the bending and twisting process is performed, the wire can slip through the bushing in order to compensate for any error in the calculation.

Figure 2:
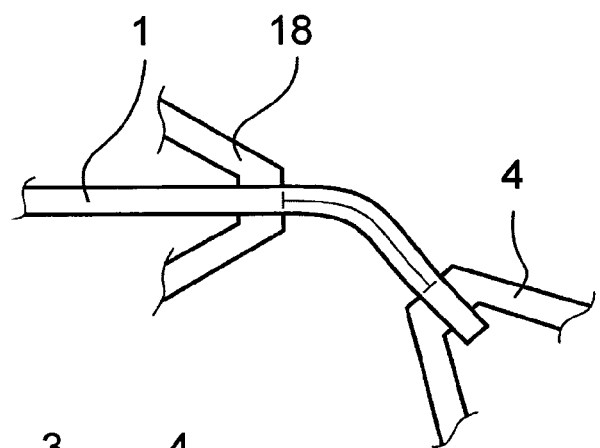
FIG. 2 illustrates how a wire is bulged if the actual consumed wire length for the bend is shorter that the calculated length represented by the original distance between the two grippers.

FIG. 1 shows a straight piece of wire 1 held by a fixed gripper 18 and a moveable gripper 4. Line 3 illustrates the calculated wire length that will be consumed for the bend according to the calculations. FIG. 2 illustrates the result of the deformation if the calculated consumed wire length is longer than the actually consumed length. The wire will show a bulge. The actual shape of the bulge depends widely on the deformation, the cross section and material of the wire, the distance between the grippers and the flexibility of the 6-axis-robot.

Figure 3:
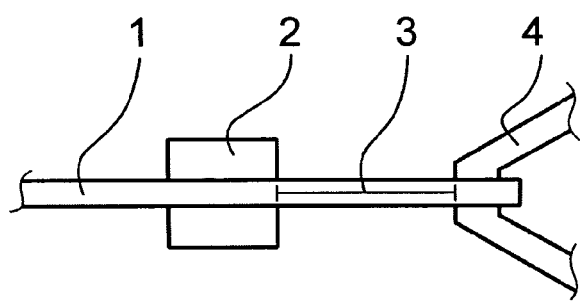
FIG. 3 illustrates a straight piece of wire being held by a bushing and a gripper. The calculated consumed wire length for the bend is indicated in the center of the wire and equals the distance between the end of the bushing and the beginning of the gripper.
Figure 4:
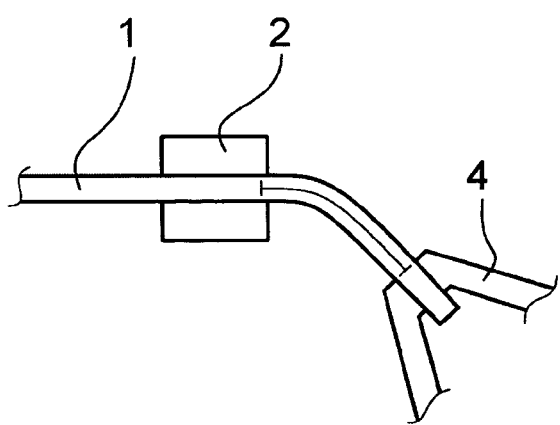
FIG. 4 illustrates that the wire has slipped through the bushing, and this wire motion has relaxed the bended portion. There is a noticeable difference between the originally calculated consumed wire length for the bend, indicated by the line in the center of the wire, and the actually consumed wire length.

FIG. 3 shows a straight piece of wire 1 supported by a bushing 2 and a moveable gripper 4. Line 3 illustrates the calculated wire length that will be consumed for the bend according to the calculations. FIG. 4 illustrates the result of the deformation. The wire 1 has slipped through bushing 2. This movement compensates the discrepancy between the calculated consumed wire length and the actually consumed length. Precise knowledge of the amount of the wire length that has slipped through the bushing is not required. For obtaining a precise wire shape, only the wire between the bushing and the gripper is relevant. The wire portion that has slipped will either add to the straight length ready to be fed for the next bends and twists or will be subtracted from that straight length, depending of the mathematical sign of the discrepancy. As long as enough straight wire length remains to be fed through the bushing for consecutive bends, the exact amount of the remaining straight wire length must not be known. Assuming that the calculations are reasonably precise, the summarized overall discrepancy between calculated and actually consumed length will not exceed 5 mm, so it is sufficient to provide a straight wire length at the beginning of the bending process showing this additional safety margin in length.

The design of the bushing must ensure low friction between the wire and its support. There are several options. One option is to have a bushing that is coated with polytetrafluoroethylene or another plastic designed for low friction bearings. Another option is to add oil to the contact surface. In both cases, the slipping movement can be also supported by temporarily applying vibrations to the bushing. This is a common approach in industrial automation when parts for instance are supposed to slide down a chute. If the parts tend to get stuck because the angle of the chute being to flat, a vibrating device is mounted to the chute. Another option is to use roller bearings. The four walls of the bushing could be substituted by eight needles that would be located at the edges of the bushing. Each needle would be pivoted by roller bearings. Also, a combination of roller bearings and plain bearings can be appropriate.

Alternative Implementation of Bending Robot According to Orthuber

Another implementation of the present invention uses a bending robot as disclosed by Orthuber et al. in U.S. Pat. No. 4,656,860. A device according to the invention has been built and distributed as part of their "bending art system" by Geyer Medizintechnik GmbH in Berlin, Germany, in close cooperation with Dr. Orthuber. The "bending art system" came complete with software for designing the wire shape and for controlling the robot. The robot as disclosed in the '860 patent consists of two characteristic design features: a bending finger (a partial cone) that can move forwards and backwards to bend the wire, and a rotating cone that can twist the wire. The wire is held during both bending and twisting operations by the outer clamping cone.

Since the robot as disclosed by Orthuber et al. in the '860 patent produces a wire consisting of straight portions, bent portions and twisted portions, it is obvious to assign straight portions to bracket slots. In other word, a specific straight portion of the wire is supposed to be located within the slot of a specific brackets slot either during treatment or at the end of treatment. The portions between two adjacent slots can be used to apply twists and bends to the wire in order to obtain a spatial shape dictated by the therapeutic task. The spatial relationship between two adjacent slots will typically be defined in mathematical terms in the numeric wire description.

The device has several restrictions. Bends and twists have to be applied to separate locations along the wire. Also, the portion of the wire extending beyond the cone is free and unconstrained, and therefore only bends over the two main axes of a cross section of a rectangular shaped wire can be applied. A bend in any direction other that one of the main axes would create side effects due to oblique bending.

Figure 6:
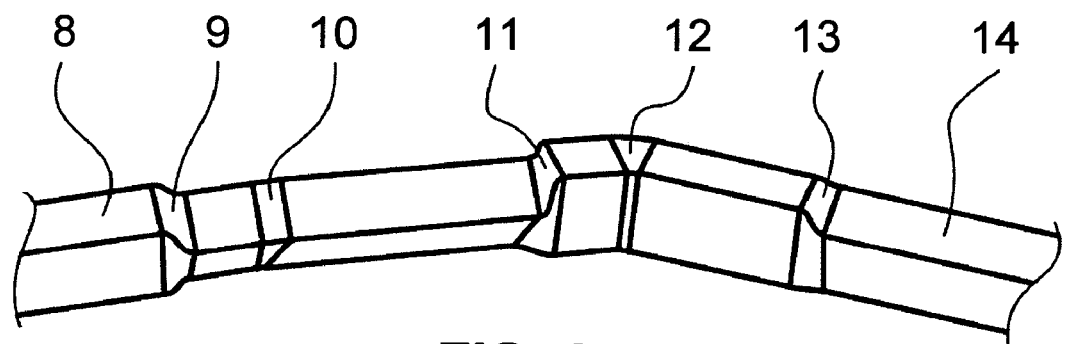
FIG. 6 is a perspective view of a wire segment that has been bent according to the classic algorithm, having two bends and three twists.

Geyer Medizintechnik GmbH has solved this problem by introducing an algorithm comprising a series of three twists and two bends. FIG. 6 shows an exemplary wire section. The wire section has two segments 8 and 14 that are assigned to bracket slots.

The relative spatial location and orientation between these two segments is therefore given. A portion of an orthodontic wire being assigned to a slot is referred to as "slot segment" in this application. Segment 8 is accordingly referred to as first slot segment and segment 14 second slot segment. Also, the bend adjacent to the first slot segment is named "first" bend. This order has been selected arbitrarily and does not imply the order of manufacturing. Basically, both slot segments have to be connected by a piece of wire. The first bend 10 can be understood as the beginning of the connecting segment, while the second bend 12 is the end of the connecting segment. In order to adjust the direction of bend 10 with respect to the orientation of the first bracket slot, a first twist 9 is required. Likewise, the third twist 13 adjusts the direction of bend 12 with respect to the orientation of the second bracket slot. Yet another twist 11 is required in order to compensate for the discrepancy of the orientation of the main axes of both bends.

While this concept represents a universal approach, it has significant disadvantages and limitations. Firstly, the distance between a bend and a twist is dictated by the design and the dimensions of the robot. The devices sold by Geyer Medizintechnik GmbH required a minimal distance of 0.7 mm between a bend and a consecutive twist and a minimal distance of 0.9 mm between a twist and a consecutive bend. It is easily understood that the series of twists and bends therefore required as much as 5 mm of wire length between adjacent brackets. This length of wire is greater than that available for closely spaced teeth, especially in lingual orthodontics.

Secondly, relevant twists are present in the wire simply to adjust the desired direction of a bend. Depending on the individual geometry, twists up to 90° can be required for a rectangular wire. In order to consume little wire length for twists, the devices sold by Geyer Medizintechnik GmbH show a distance between the twisting clamps of less than 0.3 mm. Even for ductile materials, a 90° twist applied to a wire portion shorter than the side length of the cross section is a challenge. Many materials used for orthodontic wires like shape memory alloys or beta-titanium break instantaneously when exposed to such stress.

Figure 5:
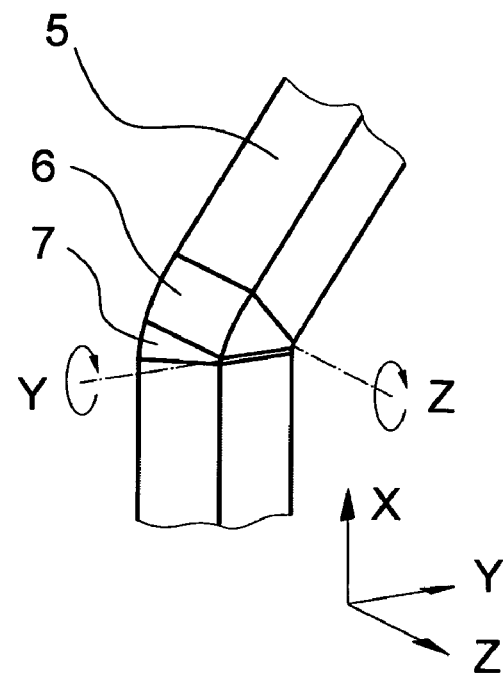
FIG. 5 is a perspective view of a piece of wire that has been bent around two axes at mainly the same wire position.

This invention introduces a new method for bending and twisting a wire using the device as disclosed in the '860 patent. Instead of applying one bend and one twist in order to adjust the direction of the bend, two bends in the directions of the two main axes are applied. Since orthodontic archwires are typically smoothly curved, following the form of the jaw, only relatively small bends are required in most cases. Even if individual adjustments are required in order to adapt a wire to a misplaced bracket or in order to re-adjust the treatment goal, the required steps in the wire are typically below 1 mm. Therefore, it is often possible to bend the wire in one direction, then turn it 90° around its longitudinal axis and apply a second bend at the same position. FIG. 5 shows a wire having two bends at one location. The bending axis for bend 7 is the Y-axis. Bend 6 has been applied around the Z-axis.

Figure 7:
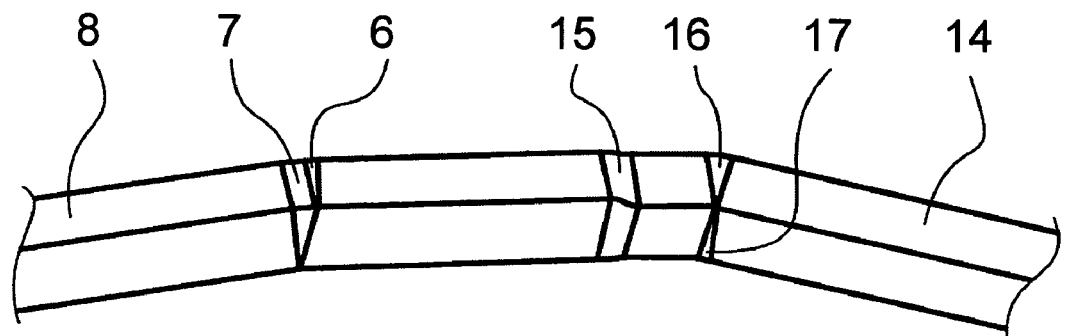
FIG. 7 is a perspective view of a wire segment that has been bent according to the method disclosed in this application, having four bends and one twist.

FIG. 7 shows the same slot segments 8 and 14 as in FIG. 6. However, bend 10 and twist 9 of FIG. 6 are substituted by bends 6 and 7. Accordingly, bend 12 and twist 13 of FIG. 6 are substituted by bends 16 and 17. Similar to the method used in FIG. 6, a twist 15 is required between the bends in order to compensate for the discrepancy of the orientation of the main axes of the bends. By comparing FIGS. 6 and 7, the advantage of the proposed method is evident. The overall length of required deformations is much shorter, and the amount of deformations is reduced. Only one twist is required, having a much lower value than required by the old method.

Figure 8A:
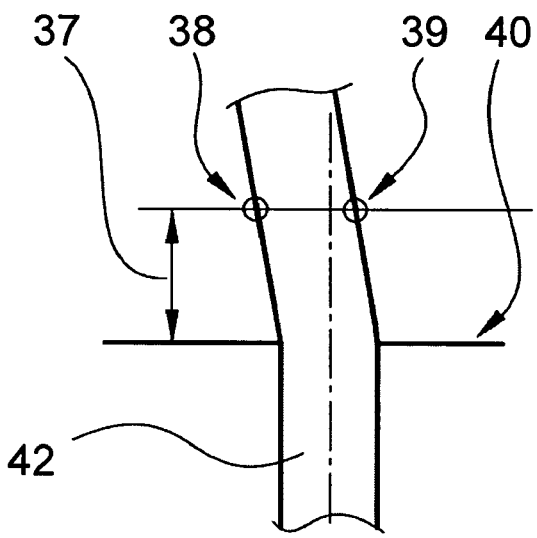
FIG. 8A is a view onto a wire that has already been bent in one direction. The end points of the line of impact for application of the second bend are located on both sides of the midline.
Figure 8B:
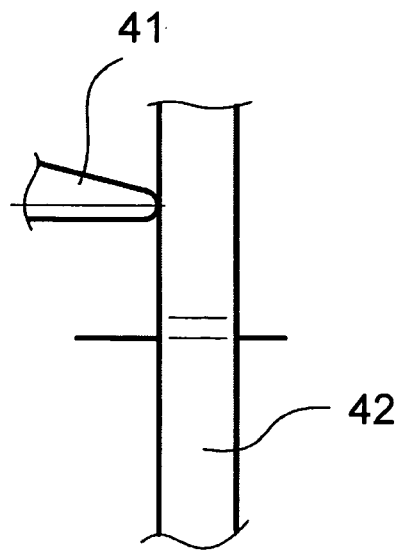
FIG. 8B is a side view onto a wire that has already been bent and illustrates the bending finger contacting the wire for the second bend.

Placing two bends at one location is possible as long as the first bend is not too large. When the bending finger of the device according to the '860 patent touches the wire, the contacting forces are applied along a line. FIG. 8A shows a wire 42 that has already been bent in one direction. Line 40 is the top edge of the outer clamping cone. The portion of the wire 42 that is extending above the cone is to be bent in the second direction. The contacting line of the bending finger has a specified height 37 above the top edge of the outer clamping cone. The robots delivered by Geyer Medizintechnik GmbH show a dimension of 0.9 mm. Both endpoints 38 and 39 of the contacting line are located on opposite sides of the center line. FIG. 8B shows a side view of the situation displayed in FIG. 8A. A forward movement of the bending finger 41 will induce a proper bend.

Figure 9:
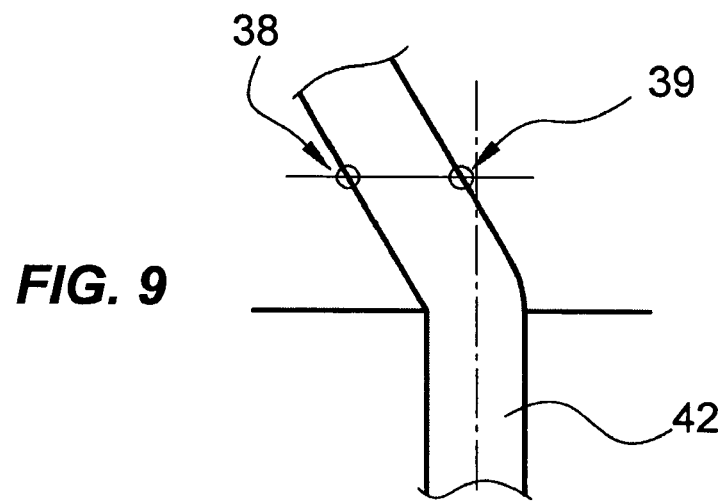
FIG. 9 is a view onto a wire that has already been bent in one direction. Both end points of the line of impact for application of the second bend are located on one side of the midline.

FIG. 9 shows a wire 42 that has a first bend of a significantly higher angle. In this case, both endpoints of the contacting line are located on the same side of the center line. A forward movement of the bending finger will also induce a twisting movement onto the wire, since both force transmission points are placed asymmetrically on one side of the center line. The result will be an undefined mixture of bend and twist. To solve this problem, the order of the bends can be changed. If the second bend is smaller, it would be useful to apply that bend first and then the other, larger bend.

In case both bends are too large, a feed motion of the wire is required before the second bend is applied. In other words, the second bend is placed a short distance away from the first bend. This does obviously consume some wire length, but is still more efficient than having a twist instead of the bend.

Figure 11:
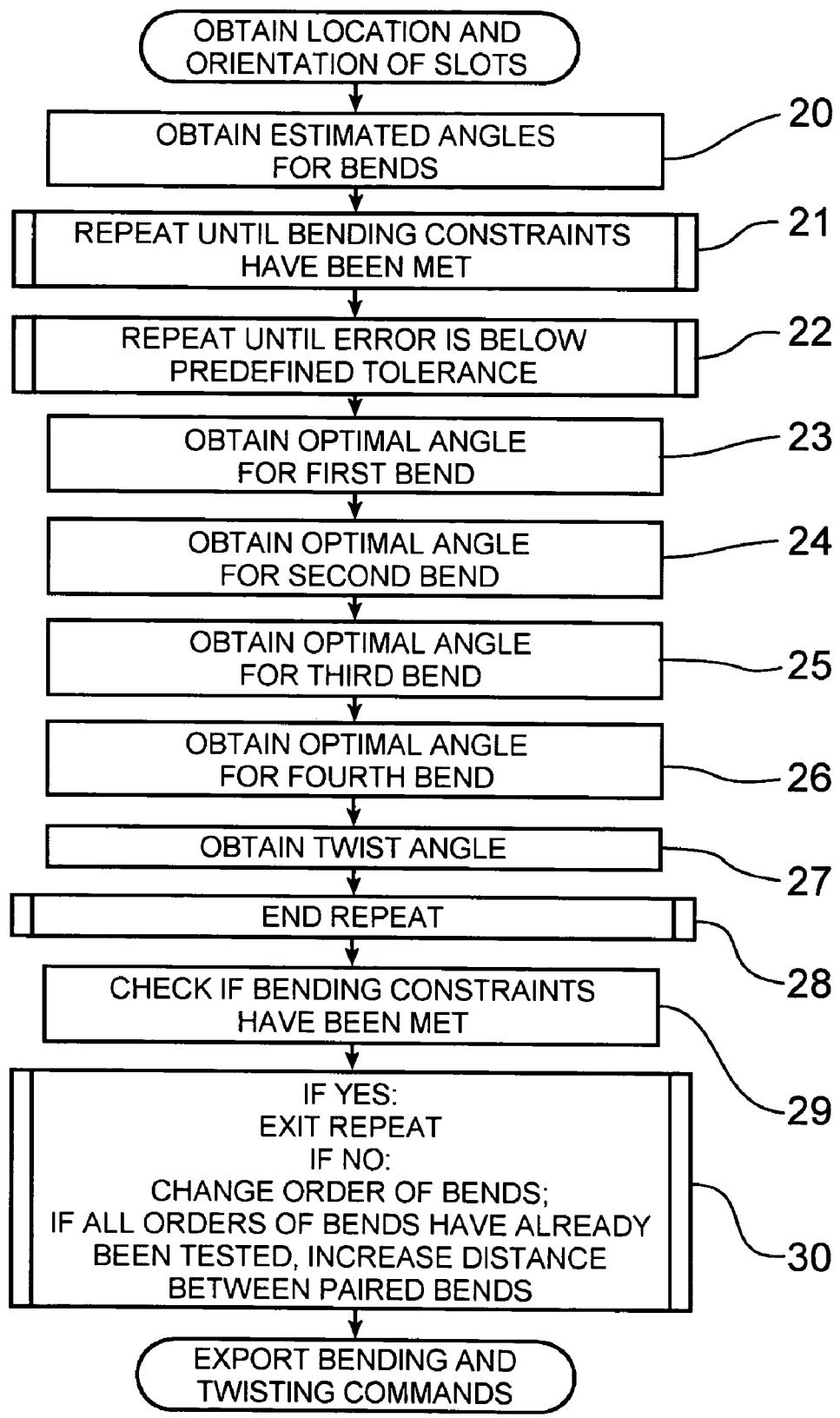
FIG. 11 is a flow diagram of calculating the required bends and twists according to the method disclosed in this application.
Figure 12:
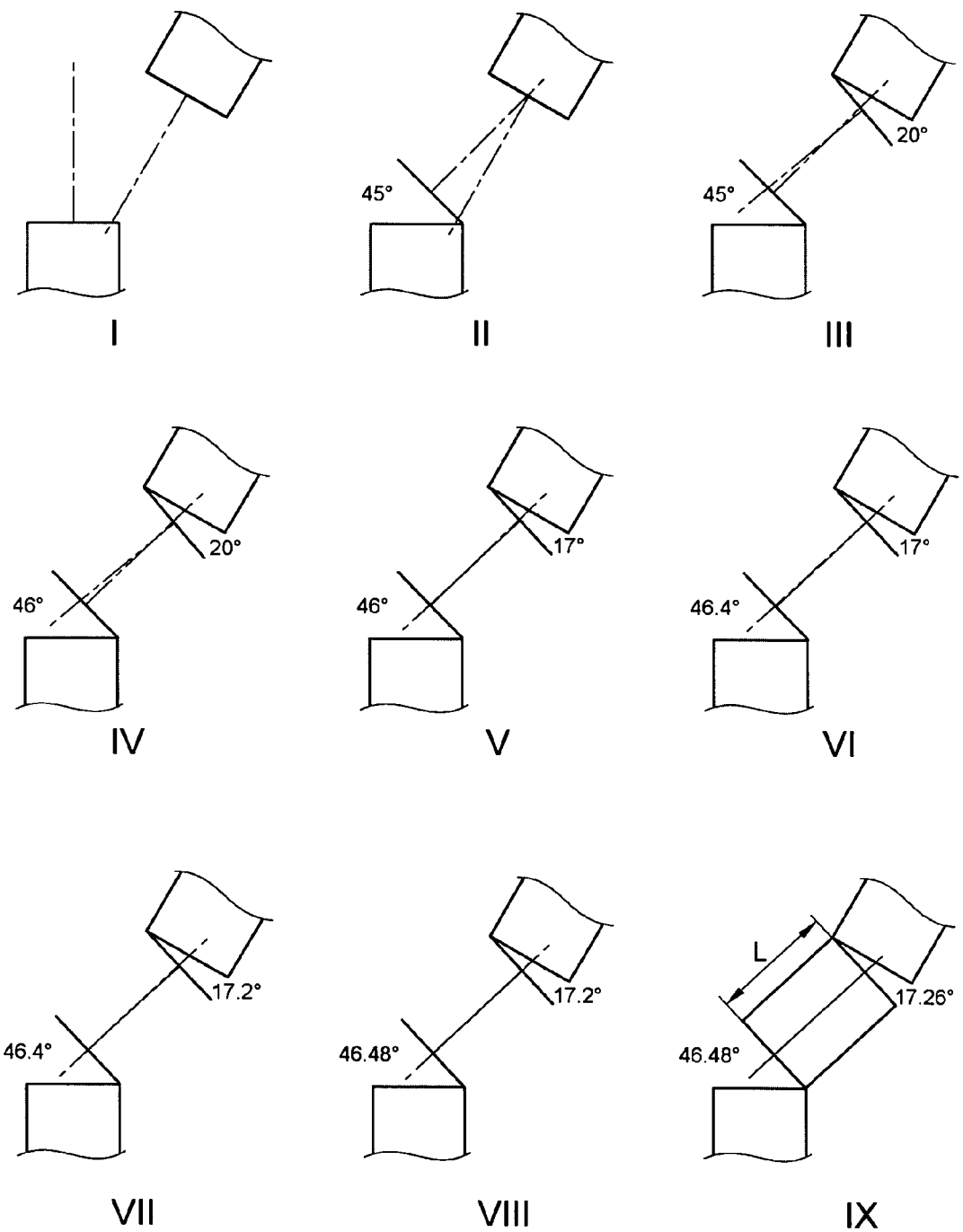
FIG. 12 displays an iterative optimization of two angles in a simplified manner.

In order to determine the required commands for the bending robot, it would be possible to use an analytic approach. Due to the various constraints and options regarding the order of bends, an iterative approach seems more adequate. FIG. 11 shows a flow chart of a preferred embodiment of method steps for calculating the command sequence for the robot. In order to obtain a good starting point for the iterative optimization, it is useful to execute step 20 and calculate four angles as starting points by virtually connecting the two slot segments by a line and projecting the connecting line onto the main planes. If this calculation is not performed, this does not have any negative effect on the end result, it just slows the calculation down by adding more iterative steps. Step 21 is the beginning of an outer loop, and step 22 is the beginning of an inner loop. In steps 23 to 26, the angles of the bends are gradually modified, together with the length of the straight wire segments (the process of gradually modifying and optimizing an angle is demonstrated in a simplified manner in FIG. 12). In step 27, the twist angle is obtained by calculating the angles between the edges of the wire segments adjacent to the twist (see segments 33 and 34 in FIG. 10). Now the remaining error is determined. One option is to calculate the normal vector for each surface terminating a segment (as shown in FIG. 12), and to determine the error in parallelism of both terminating surfaces of each segment. If a predefined value is exceeded, a new iterative loop is executed. Otherwise, the iterative loop is left (step 28). In step 29, the constraints are checked. If a bending angle is too large so that both endpoints of the contacting line of the bending finger are located on the same side of the center line, another order of bends is tested or, if all orders have been tested, the distance between paired bends is increased (step 30). In each case, a new iterative process for re-calculating the angles is required. Finally, the result is exported as ASCII file. The robots sold by Geyer Medizintechnik GmbH are fed with files having a simple format. Each line has a specific command type, indicated by a number (feed: 10; bend: 12; turn: 15; twist: 11), followed by one or more blanks and the value (with a maximum resolution of two digits after the decimal point).

Figure 10:
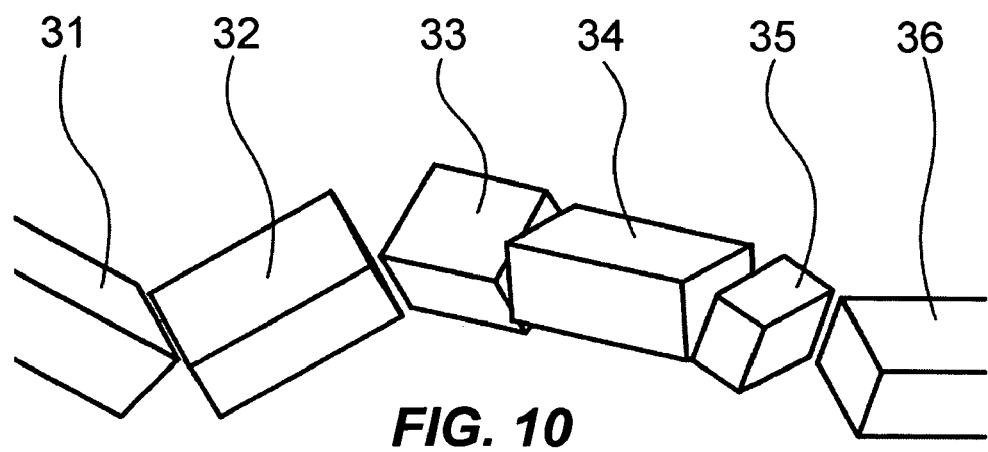
FIG. 10 is a perspective view of a group of wire segments that are connecting two slot segments according to the method disclosed in this application, having four bends and one twist.

FIG. 10 shows a perspective view of the straight segments of a wire portion extending from one slot segment 31 to the next slot segment 36. Segment 31 is followed by a bend, and the adjacent segment 32 provides the necessary distance between the two bends (both bends are very large and need to be separated from each other). Segment 32 is followed by the second bend and then by segment 33, which actually embodies one part of the connecting segment which virtually connects the slot segments. Adjacent segment 34 embodies the other part, both segments being separated respectively joined by the twist (that is displayed with a length of zero for a better understanding of the underlying geometry). Segment 34 is followed by the third bend and by another separating segment 35. The length of segment 35 is shorter because the third bending angle is much smaller than the first angle and requires less feed until the endpoints of the contact line of the bending finger are located on both sides of the center line. Segment 35 is followed by the fourth bend and is adjacent to slot segment 36.

FIG. 12 displays in a simplified manner the iterative process of optimizing angles. In this drawing, only two angles are to be optimized. Step I shows the initial situation. In step II, the first angle is optimized in a resolution of 5° in a manner that the normal vector on the angled surface passes the center of the opposite angled surface as close as possible. The result in this example is 45°. In step III, the opposite surface is optimized in the same manner, ending up with 20°. In further loops, the angles are iteratively optimized one by one, while the resolution is increased. After performing step IX, the first bend has 46.48° and the second bend 17.26°. The length L of the virtual connecting segment can also easily be calculated basing on the spatial arrangement of the two segments to be connected.

Apparatus for Bending Orthodontic Wires

In yet another implementation of the invention, an optimized apparatus is used. It has been explained earlier that the apparatus disclosed in U.S. Pat. No. 6,612,143 has the advantage of shaping the wire portion between two slot segments in one section, but the verification of the accuracy of the deformation requires significant efforts and is prone to errors. The device disclosed in U.S. Pat. No. 4,656,860 is stiff and robust, but requires up to five independent deformations to be applied one after another and has no means for a verification of the accuracy of the deformation, thus requires the use of calibrated wire materials.

This application presents a device that allows shaping a wire by applying two deformations in order to connect to slot segments. Each deformation consists of a combined bend and twist. This is achieved by clamping the wire with one moveable gripper and a fixed gripper or a fixed guiding bushing. The moveable gripper is gimbal-mounted and has three degrees of freedom. This limits the scope of deformations, but allows for a robust and stiff design of the apparatus. The stiff design is a valuable precondition for verification of the applied deformation. In a preferred embodiment, the device measures directly the resulting deformation by decoupling the gripper from any external forces and measuring the angles of the three axes with the wire dictating the spatial orientation of the gimbal axes.

Figure 13:
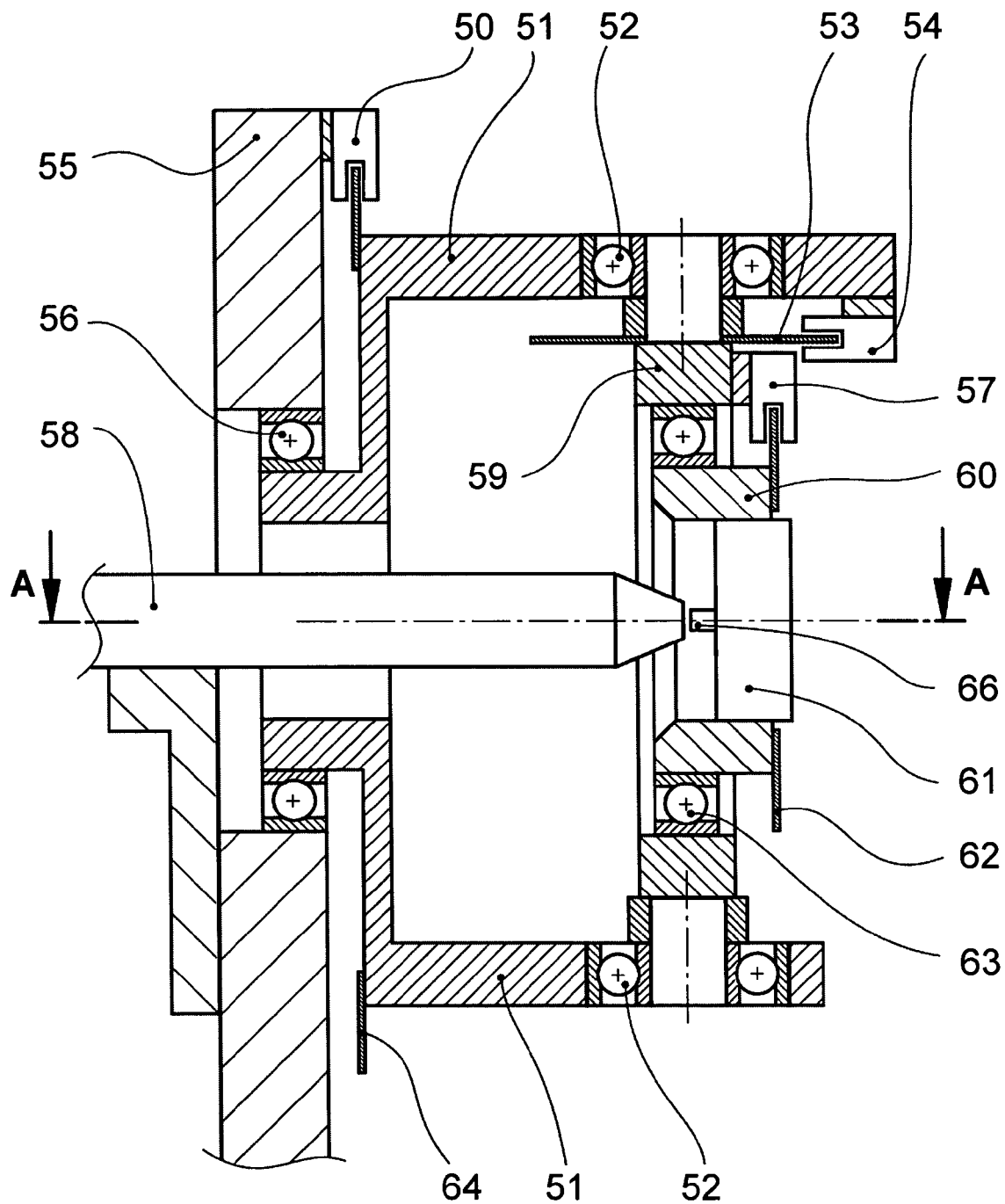
FIG. 13 is a cross-sectional view of a device for shaping orthodontic wires.

FIG. 13 shows a preferred embodiment of the invention. A wire feeding mechanism 58 is mounted to a base plate 55. A plurality of options is applicable. Friction rollers can be used as well as a mechanism which clamps the wire and moves in incremental steps. The feeding mechanism can be activated for instance by steppers or servo motors. In addition to feeding the wire, the wire feeding mechanism 58 should also mechanically guide the wire at its outlet. This is to ensure that the deformation zone of the wire is well defined and limited to the portion of the wire extending from the feed mechanism. One option to support and guide the wire would be a clamping mechanism that clamps the wire after the feeding movement is finished. Another option is a low friction bushing. This second option is favorable in light of the problems arising when the consumed length has been calculated imprecisely, and high longitudinal forces develop.

The first axis of the gimbal-mount could be named "rotational axis". The term "axis", as used in the specification and the claims, when directed to an apparatus, shall mean a configuration of means of the apparatus allowing a directed movement of portions of such means; including but not limited to rotational and translational movements.

The first axis or rotational axis is realized by ball bearing 56. The rotational base 51 can accordingly rotate around this axis, which is in line with the longitudinal wire axis of the undeformed wire inside the feeding mechanism. Rotational base 51 carries ball bearings 52, embodying the second gimbal axis that could be named "bending axis". The rotational base 51 carries also the encoding disk 64 of rotary encoder 50. Ball bearings 52 carry the bending base 59 which accordingly rotates around the bending axis. Bending base 59 holds ball bearing 63 which incorporates the third gimbal axis, the "twist axis". The names for the axes have been selected in order to improve descriptiveness. The bending base 59 carries also the encoding disk 53 of rotary encoder 54. Ball bearing 63—incorporating the twist axis—holds twist base 60. Twist base 60 carries the encoding disk 62 of rotary encoder 57. It also holds gripper unit 61. Gripper unit 61 has the task of clamping the wire with gripper fingers 66 during the deformation process and, if applicable, also during the verification process.

Again, a wide variety of design principles is applicable. Possible implementations for actuating the gripper fingers include, but are not limited to solenoids, pressurized air and electric motors.

Figure 14:
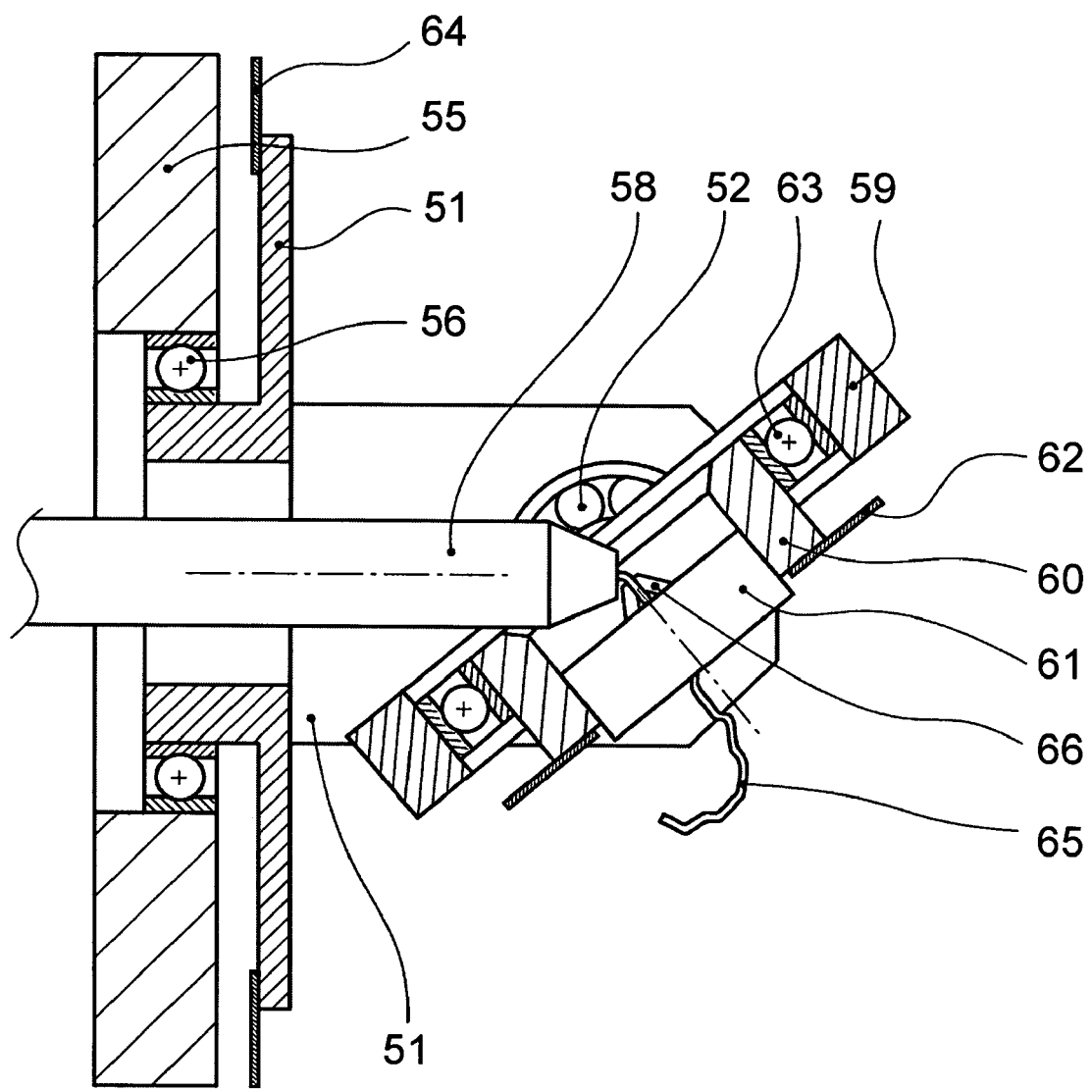
FIG. 14 is a cross-sectional top view of the device of FIG. 13, seen from view line A in FIG. 13.

FIG. 14 shows the apparatus in a cross-sectional top view. The line of view is indicated in FIG. 13 by arrows A. Deviating from FIG. 13, bending base 59 is tilted around the bending axis. Also, a wire 65 that is currently being bent is displayed. The deformation is applied to the wire zone between feeding mechanism 58 and gripper fingers 66. After the deformation is applied and, if applicable, verified, the gripper unit is released, all three gimbal axes are reset to zero, and the wire is moved forward in order to apply deformations to the next wire section.

A preferred method of operating the device is to obtain a numeric wire description similar to the one that was used by Geyer Medizintechnik GmbH to operate the robot of the '860 patent. The appropriate bends and twists that need to be applied to the wire can be calculated as described above. The main advantage of the new design is that the two bends that are placed in close proximity or at the same location can now be substituted by one bend. Since the wire is restrained on both sides of the deformation zone, an oblique bend, that is a bend where the bending axis is not identical to one of the main axes of the cross section, can be applied. The direction of the bend can be adjusted by rotating rotational base 51 to the correct position. As explained in FIGS. 7 and 10, an additional twist is typically required between two slot segments. This twist can be applied to the wire by rotating the gripper unit 61 around the twist axis. The twisting deformation is applied to the same zone as the bending deformation. With respect to the amount of torque, it is possible to apply the complete twisting angle to one deformation, but the twist can also be distributed over both deformation zones that are located between two slot segments. Temporally, the twisting deformation can be applied before the bend, simultaneously or after the bend.

The forces for bending and twisting the wire can be applied manually by an operator, or by using actuators. Applicable actuators include, but are not limited to steppers and servo motors. In a preferred environment, also the feeding mechanism 58 is controlled by a computer, so that the process of bending and twisting the wire can be fully automated.

The device as disclosed has several significant advantages. The design is simple and can be realized by using mainly inexpensive off-the-shelf components. Since only two deformations are required to shape the wire between two slot segments, the operation is much faster compared to the operation of the device of the '860 patent, where five deforming operations and several feed operations are required. Due to its stiff design and the option to have completely balanced axes with very low friction, a very reliable feedback loop for verification of the true wire shape as described below can be easily integrated.

Figure 15:
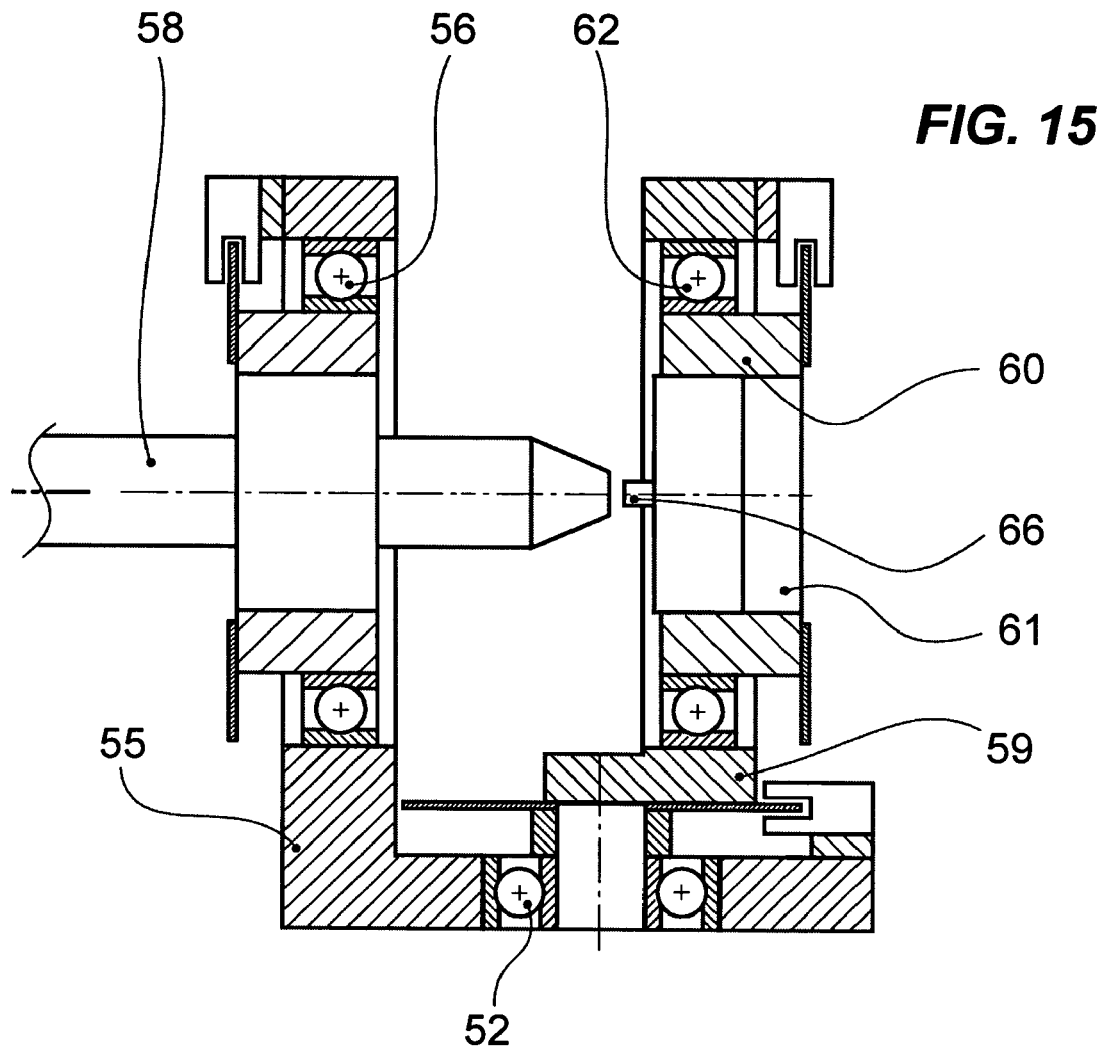
FIG. 15 displays an alternate layout of the device of FIG. 13.

FIG. 15 shows an alternate layout of the apparatus. Here, the bending axis is attached directly to base plate 55. The rotational axis is realized by mounting wire feeding mechanism 58 to bearings 56. In this way, the relative rotational movements between bending base 59 and wire feeding mechanism 58 are enabled in the same manner as in FIG. 13. The advantage of this layout is that gripper unit 61 has only two degrees of freedom with respect to the base plate. This eases routing the umbilicals for energy supply and sensor signals.

Method for Verifying the Actually Bent Shape of an Orthodontic Wire

The method disclosed in this application requires an apparatus having at least two tools that can either grip the wire or at least partially embrace the wire in order to fully adapt to the spatial position of a portion of the wire at two different locations. The term "position" as used in this specification and the claims shall mean either a location or an orientation or a combination of a location and orientation.

Then, the spatial position of each tool is measured. In order to fully reflect the orientation and location of the wire portion being held by the tool, it is important that the bearings holding the tools are designed for extra low friction. Also, no relevant external forces must be acting onto the tools. Forces like gravity must be compensated by using for instance counter weights or springs. Now only the remaining forces in the wire will drive the location and orientation of the tools. The tools will move until the wire is in its relaxed situation. If the internal damping properties of the wire material should be too low, it may be desirable to use additional damping elements in order to calm oscillations.

In a preferred embodiment, the apparatus used for the method will be an apparatus also used to bend the wire. The tools will be identical to the tools used for holding the wire when performing the desired deformation. In this way, the actual wire shape can be measured directly after the bend has been applied. This shape can be compared to the nominal shape with the help of a computer. In a preferred embodiment, the computer calculates corrective movements in order to eliminate remaining deviations from the ideal shape. These movements are executed either manually by an operator that receives respective instructions from the computer, or the computer has direct control over actuators that are coupled to the gimbal axes, and executes the necessary movements automatically. When the errors do not exceed predefined tolerances, the deformation process is regarded as successful, and the gripper is released and the gimbal axes are reset.

Figure 16:
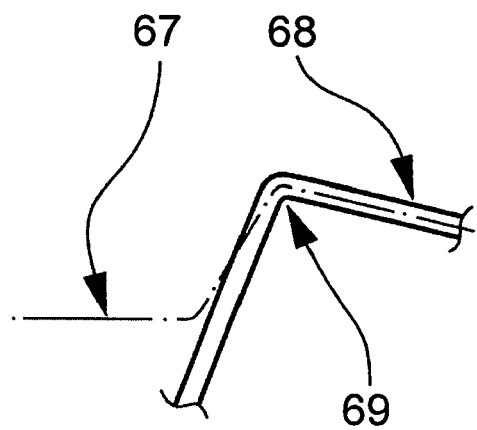
FIG. 16 displays a portion of a wire having a bend deviating from the desired angle.
Figure 17:
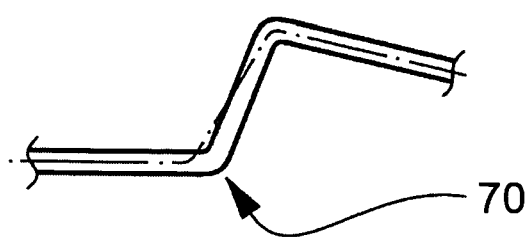
FIG. 17 displays the wire of FIG. 16 with a second bend, the second bend compensating the deviation of the first bend.

The remaining deviation of an actual bend from the nominal value can be used for recalculating the subsequent bends. FIG. 16 displays a wire 68 having a first bend 69. This bend deviates from the nominal bend represented by the nominal midline 67. FIG. 17 displays the wire after the second bend 70 has been applied. The distance between both bends has been slightly shortened, and the angle has been increased. Thus the original error in bend 69 has been compensated. Depending on the specific configuration of bends, a full compensation as demonstrated in FIGS. 16 and 17 may not be possible, but a partial compensation cane be performed. Again, the error in the second bend 70 will be measured, and a compensation of the determined deviation from the nominal value will be performed on subsequent bends.

It is obvious that an apparatus as shown in FIG. 13 or 15 with a gimbal-mounted moveable gripper is perfectly suited for measuring the actual shape of the wire. The moveable components of such an apparatus can be perfectly balanced. Also, measuring the actual angles can be performed by contact-free rotary encoders 50, 54 and 57. During the measuring process the wire is held, but no forces are applied onto the wire. In a preferred embodiment, all actuators that are used to drive the axes are completely decoupled from the axes.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

It must be understood that the illustrated embodiment has been set forth only for the purposes of example and that it should not be taken as limiting the invention. It will be apparent to those skilled in the art that alterations, other embodiments, improvements, details and uses can be made consistent with the letter and spirit of the foregoing disclosure and within the scope of this patent, which is limited only by the following claims, construed in accordance with the patent law, including the doctrine of equivalents.

In the claims which follow, reference characters used to designate claim steps are provided for convenience of description only, and are not intended to imply any particular order for performing the steps.

We claim:

1. A method of bending an orthodontic wire performed by a bending apparatus, comprising the steps of
holding a first portion of the wire with first holding means;
holding a second portion of the wire with second holding means, the second portion of the wire substantially longitudinally spaced apart from the first portion of the wire; and
performing a relative movement between the first holding means and the second holding means along at least one axis so as to place a bend in the wire having a desired configuration, the first holding means allowing substantially unrestricted longitudinal movement of the first portion of the wire at least during the process of actually deforming the wire such that the wire is pulled through the first holding means.

2. A method as defined in claim 1, further comprising the step of performing the relative movement between the first and the second holding means so as to extend the wire through the first holding means.

3. A method as defined in claim 1, wherein the method steps are performed repeatedly in a numerically controlled process so as to place at least two bends in the wire.

4. A method as defined in claim 1, wherein the relative movement is at least partially non-perpendicular relative to the longitudinal axis of the first portion of the wire.

5. A method of shaping a customized orthodontic wire and measuring the actual shape applied, comprising the steps of
holding different portions of the wire by two separate and spaced apart holding means, the holding means being moveable relatively to each other,
performing a relative movement between the two holding means by means of at least one numerically controlled actuator so as to reshape the wire to a desired configuration;
substantially isolating at least one of the two holding means from forces imposed by the at least one numerically controlled actuator; and
measuring the relative position between the two holding means.

6. A method of shaping an orthodontic wire and measuring the actual shape applied, comprising the steps of
holding different portions of the wire by two separate and spaced apart holding means, the holding means being moveable relatively to each other;
performing a relative movement between the two holding means by means of at least one numerically controlled actuator so as to reshape the wire to a desired configuration;
compensating at least partially for forces acting onto at least one of the two holding means with the exception of forces imposed by the wire; and
measuring the relative position between the two holding means.

7. An apparatus for shaping an orthodontic wire, comprising at least first and second holding means to shape a bend into the wire, the first and the second holding means each separately holding and gripping the wire at a substantially different longitudinal position of the wire, at least one of the first and second holding means allowing a substantially unrestricted longitudinal movement of the wire at least during the process of actually deforming the wire, and at least one of the holding means mounted onto a movable axis.

8. An apparatus as defined in claim 7, further comprising means for numerically controlling the position of at least one of the axes.

9. An apparatus as defined in claim 7, further comprising means for substantially isolating at least one of the axis from forces other than imposed by the wire.

10. An apparatus as defined in claim 7, further comprising means for substantially compensating forces acting onto at least one of the axes with the exception of forces imposed by the wire.

11. An apparatus as defined in claim 7, further comprising means for measuring the position of at least one of the axes.

12. An apparatus as defined in claim 7, wherein at least one of the holding means is gimbal mounted and moveable in at least two axes.

13. An apparatus as defined in claim 7, wherein two of the holding means are mounted each onto a pivoting axis allowing a rotational movement, the pivoting axes of said movements being substantially equal to the longitudinal axes of portions of the wire being held by the holding means, and wherein at least one of the pivoting axes is mounted onto another rotational axis being substantially perpendicular to both of the pivoting axes.

14. An apparatus as defined in claim 7, wherein the first holding means guides the wire and the second holding means grips the wire during the process of actually deforming the wire.

15. An apparatus as defined in claim 7, wherein the substantially unrestricted longitudinal movement of the wire is substantially unrestricted unidirectional longitudinal movement within the holding means.

16. An apparatus as defined in claim 7, wherein the at least one of the holding means mounted onto a movable axis performs at least partially a non-perpendicular movement relative to the longitudinal axis of a portion of the wire held by the first holding means.

17. An apparatus for bending an orthodontic wire, comprising:
   at least two holding means for placing a bend into the wire, at least one of the holding means allowing substantially unrestricted longitudinal movement of the wire at least during the process of actually deforming the wire, and at least one of the holding means mounted onto a moveable axis; and
   means for numerically controlling the position of at least one of the axes.

18. An apparatus for bending an orthodontic wire, comprising:
   at least two holding means for placing a bend into the wire, at least one of the holding means allowing substantially unrestricted longitudinal movement of the wire at least during the process of actually deforming the wire, and at least one of the holding means mounted onto a movable axis; and
   means for substantially isolating at least one of the axis from forces other than imposed by the wire.

19. An apparatus for bending an orthodontic wire, comprising:
   at least two holding means for placing a bend into the wire, at least one of the holding means allowing substantially unrestricted longitudinal movement of the wire at least during the process of actually deforming the wire, and at least one of the holding means mounted onto a movable axis; and
   means for substantially isolating at least one of the axis from forces other than imposed by the wire.

20. An apparatus for bending an orthodontic wire, comprising:
   at least two holding means for placing a bend into the wire, at least one of the holding means allowing substantially unrestricted longitudinal movement of the wire at least during the process of actually deforming the wire, and at least one of the holding means mounted onto a movable axis; and
   means for measuring the position of at least one of the axes.

21. An apparatus for bending an orthodontic wire, comprising at least two holding means for placing a bend into the wire, at least one of the holding means allowing substantially unrestricted longitudinal movement of the wire at least during the process of actually deforming the wire, and at least one of the holding means mounted onto a movable axis, and at least one of the holding means is gimbal mounted and moveable in at least one of the axes.

22. An apparatus for bending an orthodontic wire, comprising at least two holding means capable of placing a bend into the wire, at least one of the holding means allowing a substantially unrestricted longitudinal movement of the wire at least during the process of actually deforming the wire, two of the holding means each being mounted onto a pivoting axis allowing a rotational movement, the pivoting axes of said movements being substantially equal to the longitudinal axes of portions fo the wire being held by the holding means, at least one of the pivoting axes mounted onto another rotational axis being substantially perpendicular to both of the pivoting axes.

* * * * *